(12) United States Patent
Krizman et al.

(10) Patent No.: US 9,417,246 B2
(45) Date of Patent: Aug. 16, 2016

(54) INSULIN RECEPTOR SUBSTRATE 1 (IRS1) PROTEIN SRM/MRM ASSAY

(75) Inventors: David B. Krizman, Gaithersburg, MD (US); Todd Hembrough, Gaithersburg, MD (US); Sheeno Thyparambil, Frederick, MD (US)

(73) Assignee: EXPRESSION PATHOLOGY, INC., Rockville, MD (US)

( * ) Notice: Subject to any disclaimer, the term of this patent is extended or adjusted under 35 U.S.C. 154(b) by 117 days.

(21) Appl. No.: 13/529,902

(22) Filed: Jun. 21, 2012

(65) Prior Publication Data
US 2012/0295990 A1 Nov. 22, 2012

Related U.S. Application Data

(63) Continuation of application No. PCT/US2010/061909, filed on Dec. 22, 2010.

(60) Provisional application No. 61/289,382, filed on Dec. 22, 2009.

(51) Int. Cl.
*C12Q 1/37* (2006.01)
*G01N 33/68* (2006.01)

(52) U.S. Cl.
CPC ........ *G01N 33/6848* (2013.01); *G01N 2333/62* (2013.01); *G01N 2333/72* (2013.01)

(58) Field of Classification Search
CPC .... G01N 33/6848; G01N 33/68; G01N 33/72
See application file for complete search history.

(56) References Cited

U.S. PATENT DOCUMENTS

| | | | |
|---|---|---|---|
| 5,260,200 A * | 11/1993 | Kahn et al. | 435/69.1 |
| 7,473,532 B2 * | 1/2009 | Darfler et al. | 435/7.2 |
| 7,501,286 B2 | 3/2009 | Gygi et al. | |
| 7,632,686 B2 | 12/2009 | Anderson | |
| 2004/0023887 A1 * | 2/2004 | Pillutla et al. | 514/17 |
| 2004/0072251 A1 * | 4/2004 | Anderson | 435/7.1 |
| 2005/0163789 A9 * | 7/2005 | Durham et al. | 424/185.1 |
| 2012/0302650 A1 * | 11/2012 | Krizman et al. | 514/789 |

FOREIGN PATENT DOCUMENTS

| | | |
|---|---|---|
| EP | 2124051 A1 | 11/2009 |
| EP | 2124060 A1 | 11/2009 |
| JP | 2006105699 | 4/2006 |
| JP | 2006519996 A | 8/2006 |
| JP | 2008521907 A | 6/2008 |
| JP | 2011510306 A | 3/2011 |
| JP | 2012546213 | 5/2013 |
| WO | WO-2009002946 A1 | 12/2008 |
| WO | WO-2009092338 A1 | 7/2009 |

OTHER PUBLICATIONS

Yi et al., J. Am. Soc. Mass. Spectrom 2006, 17, 562-567.*
Groseclose et al., Proteomics 8: 3715-3724, 2008.*
Bagnato C et al.: "Proteomic Analysis of Human Coronary Atherosclerotic Plaque: A Feasibility Stury of Direct Tissue Proteomics by Liquid-Chromatography and Tandem Mass Spectrometry," The American Society for Biochemistry and Molecular Biology, Inc., Mar. 27, 2007, pp. 1-45.
Ballif B et al.: "Quantitative phosphorylation profiling of the ERK/p90 ribosomal S6 kinase-signaling cassette and its targets, the tuberous sclerosis tumor suppressors," PNAS, vol. 102, No. 3, Jan. 18, 2005, pp. 667-672.
Gerber S et al.: Absolute quantification of proteins and phosphoproteins from cell lysates by tandem MS,: PNAS, vol. 100, No. 12, Jun. 10, 2003, pp. 6940-6945.
Hawkridge A et al.: "Quantitative mass spectral evidence for the absence of circulating brain natriuretic peptie (BNP-32) in severe human heart failure," PNAS, vol. 102, No. 48, Nov. 29, 2005, pp. 17442-17447.
International Search Report and Written Opinion in International Application No. PCT/US10/61909, mailing date May 5, 2011, 10 pages.
Kazuyuk, et al: "Signaling Abnormality via Insulin Receptor Substrate and Insulin Resistance," Igaku no Ayumi, Ishiyaku Pub. fuc., Jul. 29, 2000, vol. 194, No. 5, pp. 423-430.
Koda, et al.: "Expression of Insulin Receptor Substrate 1 in Primary Breast Cancer and Lymph Node Metastases." Journal of Clinical Pathology. 2005, 58:645-649; abtract; p. 647, col. 1, para 3-4; p. 648, col. 2, para 3-4.
Li Y et al: "Mass spectrometric identification of proteotypic peptides from clinically used tumor markers", Clinical Proteomics 200806 US, vol. 4, No. 1-2, Jun. 2008, pp. 58-66.
Luo Moulun et al: "Identification of insulin receptor substrate 1 serine/threonine phosphorylation sites using mass spectrometry analysis: Regulatory role of Serine 1223", Enoocrinology, vol. 146, No. 10, Oct. 2005, pp. 4410-4416.
Wolf-Yadlin Alejandro et al: "Multiple reaction monitoring for robust quantitative proteomic analysis of cellular signaling networks", Proceedings of the National Academy of Sciences, US, vol. 104, No. 14, Apr. 1, 2007, pp. 5860-5865.
Yi Z et al: "Quantification of Phosphorylation of Insulin Receptor Substrate-1 by HPLC-ESI-MS/MS", Journal of the American Society for RMASS Spectrometry, Elsevier Science Inc, US, vol. 17, No. 4, Apr. 1, 2006, pp. 562-567.
Extended European Search Report in Application No. 108435918, mailing date Jun. 18, 2013, 14 pages.

* cited by examiner

*Primary Examiner* — Gyan Chandra
(74) *Attorney, Agent, or Firm* — Perkins Coie LLP

(57) ABSTRACT

The current disclosure provides for specific peptides from the Insulin Receptor Substrate 1 (IRS1) protein and the derived ionization characteristics of those peptides that are advantageous for quantifying IRS1 directly in formalin fixed biological samples by the method of Selected Reaction Monitoring (SRM) mass spectrometry. Such fixed biological samples include: formalin-fixed tissue/cells, formalin-fixed/paraffin embedded (FFPE) tissue/cells, FFPE tissue blocks and cells from those blocks, and formalin fixed and paraffin embedded tissue culture cells. IRS1 protein is quantitated in biological samples by the method of SRM/MRM mass spectrometry by quantitating one or more of the peptides described herein. The peptides can be quantitated if they reside in a modified or an unmodified form. Examples of potentially modified forms of IRS1 peptides include those bearing phosphorylation of a tyrosine, threonine, serine, and/or other amino acid residues within the peptide sequence.

3 Claims, No Drawings

SEQUENCE LISTING

<160> NUMBER OF SEQ ID NOS: 77

<210> SEQ ID NO 1
<211> LENGTH: 16

-continued

```
<212> TYPE: PRT
<213> ORGANISM: Artificial Sequence
<220> FEATURE:
<223> OTHER INFORMATION: IRS Peptide

<400> SEQUENCE: 1

Glu Val Trp Gln Val Ile Leu Lys Pro Lys Gly Leu Gly Gln Thr Lys
1               5                   10                  15

<210> SEQ ID NO 2
<211> LENGTH: 19
<212> TYPE: PRT
<213> ORGANISM: Artificial Sequence
<220> FEATURE:
<223> OTHER INFORMATION: IRS Peptide

<400> SEQUENCE: 2

Gly Leu Gly Gln Thr Lys Asn Leu Ile Gly Ile Tyr Arg Leu Cys Leu
1               5                   10                  15

Thr Ser Lys

<210> SEQ ID NO 3
<211> LENGTH: 24
<212> TYPE: PRT
<213> ORGANISM: Artificial Sequence
<220> FEATURE:
<223> OTHER INFORMATION: IRS Peptide

<400> SEQUENCE: 3

Gly Ser Gly Asp Tyr Met Pro Met Ser Pro Lys Ser Val Ser Ala Pro
1               5                   10                  15

Gln Gln Ile Ile Asn Pro Ile Arg
            20

<210> SEQ ID NO 4
<211> LENGTH: 21
<212> TYPE: PRT
<213> ORGANISM: Artificial Sequence
<220> FEATURE:
<223> OTHER INFORMATION: IRS Peptide

<400> SEQUENCE: 4

Leu Cys Gly Ala Ala Gly Gly Leu Glu Asn Gly Leu Asn Tyr Ile Asp
1               5                   10                  15

Leu Asp Leu Val Lys
            20

<210> SEQ ID NO 5
<211> LENGTH: 17
<212> TYPE: PRT
<213> ORGANISM: Artificial Sequence
<220> FEATURE:
<223> OTHER INFORMATION: IRS Peptide

<400> SEQUENCE: 5

Leu Asn Ser Glu Ala Ala Ala Val Val Leu Gln Leu Met Asn Ile Arg
1               5                   10                  15

Arg

<210> SEQ ID NO 6
<211> LENGTH: 18
<212> TYPE: PRT
<213> ORGANISM: Artificial Sequence
<220> FEATURE:
<223> OTHER INFORMATION: IRS Peptide
```

-continued

```
<400> SEQUENCE: 6

Leu Trp Thr Asn Gly Val Gly Gly His His Ser His Val Leu Pro His
1               5                   10                  15

Pro Lys

<210> SEQ ID NO 7
<211> LENGTH: 10
<212> TYPE: PRT
<213> ORGANISM: Artificial Sequence
<220> FEATURE:
<223> OTHER INFORMATION: IRS Peptide

<400> SEQUENCE: 7

Asn Lys His Leu Val Ala Leu Tyr Thr Arg
1               5                   10

<210> SEQ ID NO 8
<211> LENGTH: 15
<212> TYPE: PRT
<213> ORGANISM: Artificial Sequence
<220> FEATURE:
<223> OTHER INFORMATION: IRS Peptide

<400> SEQUENCE: 8

Pro Lys Gly Leu Gly Gln Thr Lys Asn Leu Ile Gly Ile Tyr Arg
1               5                   10                  15

<210> SEQ ID NO 9
<211> LENGTH: 13
<212> TYPE: PRT
<213> ORGANISM: Artificial Sequence
<220> FEATURE:
<223> OTHER INFORMATION: IRS Peptide

<400> SEQUENCE: 9

Arg Ser Ile Pro Leu Glu Ser Cys Phe Asn Ile Asn Lys
1               5                   10

<210> SEQ ID NO 10
<211> LENGTH: 15
<212> TYPE: PRT
<213> ORGANISM: Artificial Sequence
<220> FEATURE:
<223> OTHER INFORMATION: IRS Peptide

<400> SEQUENCE: 10

Arg Thr His Ser Ala Gly Thr Ser Pro Thr Ile Thr His Gln Lys
1               5                   10                  15

<210> SEQ ID NO 11
<211> LENGTH: 32
<212> TYPE: PRT
<213> ORGANISM: Artificial Sequence
<220> FEATURE:
<223> OTHER INFORMATION: IRS Peptide

<400> SEQUENCE: 11

Ser Gln Ser Ser Ser Asn Cys Ser Asn Pro Ile Ser Val Pro Leu Arg
1               5                   10                  15

Arg His His Leu Asn Asn Pro Pro Ser Gln Val Gly Leu Thr Arg
                20                  25                  30

<210> SEQ ID NO 12
<211> LENGTH: 14
```

```
<212> TYPE: PRT
<213> ORGANISM: Artificial Sequence
<220> FEATURE:
<223> OTHER INFORMATION: IRS Peptide

<400> SEQUENCE: 12

Ser Val Ser Ala Pro Gln Gln Ile Ile Asn Pro Ile Arg Arg
1               5                   10

<210> SEQ ID NO 13
<211> LENGTH: 22
<212> TYPE: PRT
<213> ORGANISM: Artificial Sequence
<220> FEATURE:
<223> OTHER INFORMATION: IRS Peptide

<400> SEQUENCE: 13

Thr Ile Ser Phe Val Lys Leu Asn Ser Glu Ala Ala Val Val Leu
1               5                   10                  15

Gln Leu Met Asn Ile Arg
            20

<210> SEQ ID NO 14
<211> LENGTH: 13
<212> TYPE: PRT
<213> ORGANISM: Artificial Sequence
<220> FEATURE:
<223> OTHER INFORMATION: IRS Peptide

<400> SEQUENCE: 14

Val Asp Thr Ala Ala Gln Thr Asn Ser Arg Leu Ala Arg
1               5                   10

<210> SEQ ID NO 15
<211> LENGTH: 11
<212> TYPE: PRT
<213> ORGANISM: Artificial Sequence
<220> FEATURE:
<223> OTHER INFORMATION: IRS Peptide

<400> SEQUENCE: 15

Val Ile Arg Ala Asp Pro Gln Gly Cys Arg Arg
1               5                   10

<210> SEQ ID NO 16
<211> LENGTH: 18
<212> TYPE: PRT
<213> ORGANISM: Artificial Sequence
<220> FEATURE:
<223> OTHER INFORMATION: IRS Peptide

<400> SEQUENCE: 16

Ala Ala Ser Glu Ala Gly Gly Pro Ala Arg Leu Glu Tyr Tyr Glu Asn
1               5                   10                  15

Glu Lys

<210> SEQ ID NO 17
<211> LENGTH: 13
<212> TYPE: PRT
<213> ORGANISM: Artificial Sequence
<220> FEATURE:
<223> OTHER INFORMATION: IRS Peptide

<400> SEQUENCE: 17

Ala Ala Trp Gln Glu Ser Thr Gly Val Glu Met Gly Arg
1               5                   10
```

<210> SEQ ID NO 18
<211> LENGTH: 26
<212> TYPE: PRT
<213> ORGANISM: Artificial Sequence
<220> FEATURE:
<223> OTHER INFORMATION: IRS Peptide

<400> SEQUENCE: 18

```
Ala Ala Trp Gln Glu Ser Thr Gly Val Glu Met Gly Arg Leu Gly Pro
1               5                   10                  15

Ala Pro Pro Gly Ala Ala Ser Ile Cys Arg
            20                  25
```

<210> SEQ ID NO 19
<211> LENGTH: 7
<212> TYPE: PRT
<213> ORGANISM: Artificial Sequence
<220> FEATURE:
<223> OTHER INFORMATION: IRS Peptide

<400> SEQUENCE: 19

```
Ala Asp Pro Gln Gly Cys Arg
1               5
```

<210> SEQ ID NO 20
<211> LENGTH: 11
<212> TYPE: PRT
<213> ORGANISM: Artificial Sequence
<220> FEATURE:
<223> OTHER INFORMATION: IRS Peptide

<400> SEQUENCE: 20

```
Ala Met Ser Asp Glu Phe Arg Pro Arg Ser Lys
1               5                   10
```

<210> SEQ ID NO 21
<211> LENGTH: 18
<212> TYPE: PRT
<213> ORGANISM: Artificial Sequence
<220> FEATURE:
<223> OTHER INFORMATION: IRS Peptide

<400> SEQUENCE: 21

```
Ala Arg Glu Gln Gln Gln Gln Gln Gln Pro Leu Leu His Pro Pro Glu
1               5                   10                  15

Pro Lys
```

<210> SEQ ID NO 22
<211> LENGTH: 26
<212> TYPE: PRT
<213> ORGANISM: Artificial Sequence
<220> FEATURE:
<223> OTHER INFORMATION: IRS Peptide

<400> SEQUENCE: 22

```
Ala Ser Ser Asp Gly Glu Gly Thr Met Ser Arg Pro Ala Ser Val Asp
1               5                   10                  15

Gly Ser Pro Val Ser Pro Ser Thr Asn Arg
            20                  25
```

<210> SEQ ID NO 23
<211> LENGTH: 10
<212> TYPE: PRT
<213> ORGANISM: Artificial Sequence

```
<220> FEATURE:
<223> OTHER INFORMATION: IRS Peptide

<400> SEQUENCE: 23

Cys Pro Ser Gln Leu Gln Pro Ala Pro Arg
1               5                   10

<210> SEQ ID NO 24
<211> LENGTH: 11
<212> TYPE: PRT
<213> ORGANISM: Artificial Sequence
<220> FEATURE:
<223> OTHER INFORMATION: IRS Peptide

<400> SEQUENCE: 24

Glu Glu Glu Thr Gly Thr Glu Glu Tyr Met Lys
1               5                   10

<210> SEQ ID NO 25
<211> LENGTH: 27
<212> TYPE: PRT
<213> ORGANISM: Artificial Sequence
<220> FEATURE:
<223> OTHER INFORMATION: IRS Peptide

<400> SEQUENCE: 25

Cys Thr Pro Gly Thr Gly Leu Gly Thr Ser Pro Ala Leu Ala Gly Asp
1               5                   10                  15

Glu Ala Ser Ala Ala Asp Leu Asp Asn Arg
            20                  25

<210> SEQ ID NO 26
<211> LENGTH: 8
<212> TYPE: PRT
<213> ORGANISM: Artificial Sequence
<220> FEATURE:
<223> OTHER INFORMATION: IRS Peptide

<400> SEQUENCE: 26

Met Asp Leu Gly Pro Gly Arg Arg
1               5

<210> SEQ ID NO 27
<211> LENGTH: 15
<212> TYPE: PRT
<213> ORGANISM: Artificial Sequence
<220> FEATURE:
<223> OTHER INFORMATION: IRS Peptide

<400> SEQUENCE: 27

Phe Phe Val Leu Arg Ala Ala Ser Glu Ala Gly Gly Pro Ala Arg
1               5                   10                  15

<210> SEQ ID NO 28
<211> LENGTH: 33
<212> TYPE: PRT
<213> ORGANISM: Artificial Sequence
<220> FEATURE:
<223> OTHER INFORMATION: IRS Peptide

<400> SEQUENCE: 28

Gly Gly Asn Gly His Arg Cys Thr Pro Gly Thr Gly Leu Gly Thr Ser
1               5                   10                  15

Pro Ala Leu Ala Gly Asp Glu Ala Ala Ser Ala Ala Asp Leu Asp Asn
            20                  25                  30
```

Arg

<210> SEQ ID NO 29
<211> LENGTH: 15
<212> TYPE: PRT
<213> ORGANISM: Artificial Sequence
<220> FEATURE:
<223> OTHER INFORMATION: IRS Peptide

<400> SEQUENCE: 29

His His Leu Asn Asn Pro Pro Ser Gln Val Gly Leu Thr Arg
1               5                   10                  15

<210> SEQ ID NO 30
<211> LENGTH: 22
<212> TYPE: PRT
<213> ORGANISM: Artificial Sequence
<220> FEATURE:
<223> OTHER INFORMATION: IRS Peptide

<400> SEQUENCE: 30

His Ser Ala Phe Val Pro Thr Arg Ser Tyr Pro Glu Glu Gly Leu Glu
1               5                   10                  15

Met His Pro Leu Glu Arg
            20

<210> SEQ ID NO 31
<211> LENGTH: 11
<212> TYPE: PRT
<213> ORGANISM: Artificial Sequence
<220> FEATURE:
<223> OTHER INFORMATION: IRS Peptide

<400> SEQUENCE: 31

Gly Ser Gly Asp Tyr Met Pro Met Ser Pro Lys
1               5                   10

<210> SEQ ID NO 32
<211> LENGTH: 10
<212> TYPE: PRT
<213> ORGANISM: Artificial Sequence
<220> FEATURE:
<223> OTHER INFORMATION: IRS Peptide

<400> SEQUENCE: 32

Val Asp Thr Ala Ala Gln Thr Asn Ser Arg
1               5                   10

<210> SEQ ID NO 33
<211> LENGTH: 7
<212> TYPE: PRT
<213> ORGANISM: Artificial Sequence
<220> FEATURE:
<223> OTHER INFORMATION: IRS Peptide

<400> SEQUENCE: 33

Lys Val Gly Tyr Leu Arg Lys
1               5

<210> SEQ ID NO 34
<211> LENGTH: 13
<212> TYPE: PRT
<213> ORGANISM: Artificial Sequence
<220> FEATURE:
<223> OTHER INFORMATION: IRS Peptide

<400> SEQUENCE: 34

```
Leu Ala Arg Pro Thr Arg Leu Ser Leu Gly Asp Pro Lys
1               5                   10

<210> SEQ ID NO 35
<211> LENGTH: 46
<212> TYPE: PRT
<213> ORGANISM: Artificial Sequence
<220> FEATURE:
<223> OTHER INFORMATION: IRS Peptide

<400> SEQUENCE: 35

Leu His Pro Pro Leu Asn His Ser Arg Ser Ile Pro Met Pro Ala Ser
1               5                   10                  15

Arg Cys Ser Pro Ser Ala Thr Ser Pro Val Ser Leu Ser Ser Ser Ser
                20                  25                  30

Thr Ser Gly His Gly Ser Thr Ser Asp Cys Leu Phe Pro Arg
            35                  40                  45

<210> SEQ ID NO 36
<211> LENGTH: 27
<212> TYPE: PRT
<213> ORGANISM: Artificial Sequence
<220> FEATURE:
<223> OTHER INFORMATION: IRS Peptide

<400> SEQUENCE: 36

Leu Leu Tyr Ala Ala Thr Ala Asp Asp Ser Ser Ser Thr Ser Ser
1               5                   10                  15

Asp Ser Leu Gly Gly Gly Tyr Cys Gly Ala Arg
                20                  25

<210> SEQ ID NO 37
<211> LENGTH: 13
<212> TYPE: PRT
<213> ORGANISM: Artificial Sequence
<220> FEATURE:
<223> OTHER INFORMATION: IRS Peptide

<400> SEQUENCE: 37

Leu Ser Leu Gly Asp Pro Lys Ala Ser Thr Leu Pro Arg
1               5                   10

<210> SEQ ID NO 38
<211> LENGTH: 7
<212> TYPE: PRT
<213> ORGANISM: Artificial Sequence
<220> FEATURE:
<223> OTHER INFORMATION: IRS Peptide

<400> SEQUENCE: 38

Leu Ser Thr Ser Ser Gly Arg
1               5

<210> SEQ ID NO 39
<211> LENGTH: 20
<212> TYPE: PRT
<213> ORGANISM: Artificial Sequence
<220> FEATURE:
<223> OTHER INFORMATION: IRS Peptide

<400> SEQUENCE: 39

Pro Ala Ser Val Asp Gly Ser Pro Val Ser Pro Ser Thr Asn Arg Thr
1               5                   10                  15

His Ala His Arg
```

20

<210> SEQ ID NO 40
<211> LENGTH: 26
<212> TYPE: PRT
<213> ORGANISM: Artificial Sequence
<220> FEATURE:
<223> OTHER INFORMATION: IRS Peptide

<400> SEQUENCE: 40

Pro Asp Ser Ser Thr Leu His Thr Asp Asp Gly Tyr Met Pro Met Ser
1               5                   10                  15

Pro Gly Val Ala Pro Val Pro Ser Gly Arg
            20                  25

<210> SEQ ID NO 41
<211> LENGTH: 9
<212> TYPE: PRT
<213> ORGANISM: Artificial Sequence
<220> FEATURE:
<223> OTHER INFORMATION: IRS Peptide

<400> SEQUENCE: 41

Pro Gly Glu Leu Gly Gly Ala Pro Lys
1               5

<210> SEQ ID NO 42
<211> LENGTH: 20
<212> TYPE: PRT
<213> ORGANISM: Artificial Sequence
<220> FEATURE:
<223> OTHER INFORMATION: IRS Peptide

<400> SEQUENCE: 42

Pro Arg Ser Lys Ser Gln Ser Ser Ser Asn Cys Ser Asn Pro Ile Ser
1               5                   10                  15

Val Pro Leu Arg
            20

<210> SEQ ID NO 43
<211> LENGTH: 16
<212> TYPE: PRT
<213> ORGANISM: Artificial Sequence
<220> FEATURE:
<223> OTHER INFORMATION: IRS Peptide

<400> SEQUENCE: 43

Pro Thr Arg Leu Ser Leu Gly Asp Pro Lys Ala Ser Thr Leu Pro Arg
1               5                   10                  15

<210> SEQ ID NO 44
<211> LENGTH: 18
<212> TYPE: PRT
<213> ORGANISM: Artificial Sequence
<220> FEATURE:
<223> OTHER INFORMATION: IRS Peptide

<400> SEQUENCE: 44

Gln Ser Tyr Val Asp Thr Ser Pro Ala Ala Pro Val Ser Tyr Ala Asp
1               5                   10                  15

Met Arg

<210> SEQ ID NO 45
<211> LENGTH: 16
<212> TYPE: PRT

```
<213> ORGANISM: Artificial Sequence
<220> FEATURE:
<223> OTHER INFORMATION: IRS Peptide

<400> SEQUENCE: 45

Arg His His Leu Asn Asn Pro Pro Pro Ser Gln Val Gly Leu Thr Arg
1               5                   10                  15

<210> SEQ ID NO 46
<211> LENGTH: 14
<212> TYPE: PRT
<213> ORGANISM: Artificial Sequence
<220> FEATURE:
<223> OTHER INFORMATION: IRS Peptide

<400> SEQUENCE: 46

His Ser Ser Glu Thr Phe Ser Ser Thr Pro Ser Ala Thr Arg
1               5                   10

<210> SEQ ID NO 47
<211> LENGTH: 19
<212> TYPE: PRT
<213> ORGANISM: Artificial Sequence
<220> FEATURE:
<223> OTHER INFORMATION: IRS Peptide

<400> SEQUENCE: 47

Arg Ser Arg Thr Glu Ser Ile Thr Ala Thr Ser Pro Ala Ser Met Val
1               5                   10                  15

Gly Gly Lys

<210> SEQ ID NO 48
<211> LENGTH: 16
<212> TYPE: PRT
<213> ORGANISM: Artificial Sequence
<220> FEATURE:
<223> OTHER INFORMATION: IRS Peptide

<400> SEQUENCE: 48

Arg Ser Ser Glu Asp Leu Ser Ala Tyr Ala Ser Ile Ser Phe Gln Lys
1               5                   10                  15

<210> SEQ ID NO 49
<211> LENGTH: 12
<212> TYPE: PRT
<213> ORGANISM: Artificial Sequence
<220> FEATURE:
<223> OTHER INFORMATION: IRS Peptide

<400> SEQUENCE: 49

Ser Ile Pro Leu Glu Ser Cys Phe Asn Ile Asn Lys
1               5                   10

<210> SEQ ID NO 50
<211> LENGTH: 18
<212> TYPE: PRT
<213> ORGANISM: Artificial Sequence
<220> FEATURE:
<223> OTHER INFORMATION: IRS Peptide

<400> SEQUENCE: 50

Ser Lys Ser Gln Ser Ser Ser Asn Cys Ser Asn Pro Ile Ser Val Pro
1               5                   10                  15

Leu Arg
```

```
<210> SEQ ID NO 51
<211> LENGTH: 18
<212> TYPE: PRT
<213> ORGANISM: Artificial Sequence
<220> FEATURE:
<223> OTHER INFORMATION: IRS Peptide

<400> SEQUENCE: 51

Ser Arg Thr Glu Ser Ile Thr Ala Thr Ser Pro Ala Ser Met Val Gly
1               5                   10                  15

Gly Lys

<210> SEQ ID NO 52
<211> LENGTH: 28
<212> TYPE: PRT
<213> ORGANISM: Artificial Sequence
<220> FEATURE:
<223> OTHER INFORMATION: IRS Peptide

<400> SEQUENCE: 52

Ser Ser Ala Ser Val Ser Gly Ser Pro Ser Asp Gly Gly Phe Ile Ser
1               5                   10                  15

Ser Asp Glu Tyr Gly Ser Ser Pro Cys Asp Phe Arg
            20                  25

<210> SEQ ID NO 53
<211> LENGTH: 20
<212> TYPE: PRT
<213> ORGANISM: Artificial Sequence
<220> FEATURE:
<223> OTHER INFORMATION: IRS Peptide

<400> SEQUENCE: 53

Ser Ser Glu Asp Leu Ser Ala Tyr Ala Ser Ile Ser Phe Gln Lys Gln
1               5                   10                  15

Pro Glu Asp Arg
            20

<210> SEQ ID NO 54
<211> LENGTH: 17
<212> TYPE: PRT
<213> ORGANISM: Artificial Sequence
<220> FEATURE:
<223> OTHER INFORMATION: IRS Peptide

<400> SEQUENCE: 54

Ser Ser Phe Arg Ser Val Thr Pro Asp Ser Leu Gly His Thr Pro Pro
1               5                   10                  15

Ala

<210> SEQ ID NO 55
<211> LENGTH: 14
<212> TYPE: PRT
<213> ORGANISM: Artificial Sequence
<220> FEATURE:
<223> OTHER INFORMATION: IRS Peptide

<400> SEQUENCE: 55

Gly Glu Glu Glu Leu Ser Asn Tyr Ile Cys Met Gly Gly Lys
1               5                   10

<210> SEQ ID NO 56
<211> LENGTH: 14
<212> TYPE: PRT
<213> ORGANISM: Artificial Sequence
```

<220> FEATURE:
<223> OTHER INFORMATION: IRS Peptide

<400> SEQUENCE: 56

Ser Val Thr Pro Asp Ser Leu Gly His Thr Pro Pro Ala Arg
1               5                   10

<210> SEQ ID NO 57
<211> LENGTH: 14
<212> TYPE: PRT
<213> ORGANISM: Artificial Sequence
<220> FEATURE:
<223> OTHER INFORMATION: IRS Peptide

<400> SEQUENCE: 57

Ser Tyr Pro Glu Glu Gly Leu Glu Met His Pro Leu Glu Arg
1               5                   10

<210> SEQ ID NO 58
<211> LENGTH: 16
<212> TYPE: PRT
<213> ORGANISM: Artificial Sequence
<220> FEATURE:
<223> OTHER INFORMATION: IRS Peptide

<400> SEQUENCE: 58

Thr Glu Ser Ile Thr Ala Thr Ser Pro Ala Ser Met Val Gly Gly Lys
1               5                   10                  15

<210> SEQ ID NO 59
<211> LENGTH: 27
<212> TYPE: PRT
<213> ORGANISM: Artificial Sequence
<220> FEATURE:
<223> OTHER INFORMATION: IRS Peptide

<400> SEQUENCE: 59

Val Gly Asn Thr Val Pro Phe Gly Ala Gly Ala Ala Val Gly Gly Gly
1               5                   10                  15

Gly Gly Ser Ser Ser Ser Ser Glu Asp Val Lys
            20                  25

<210> SEQ ID NO 60
<211> LENGTH: 12
<212> TYPE: PRT
<213> ORGANISM: Artificial Sequence
<220> FEATURE:
<223> OTHER INFORMATION: IRS Peptide

<400> SEQUENCE: 60

Val Asn Leu Ser Pro Asn Arg Asn Gln Ser Ala Lys
1               5                   10

<210> SEQ ID NO 61
<211> LENGTH: 11
<212> TYPE: PRT
<213> ORGANISM: Artificial Sequence
<220> FEATURE:
<223> OTHER INFORMATION: IRS Peptide

<400> SEQUENCE: 61

Gly Ser Gly Asp Tyr Met Pro Met Ser Pro Lys
1               5                   10

<210> SEQ ID NO 62
<211> LENGTH: 26

<212> TYPE: PRT
<213> ORGANISM: Artificial Sequence
<220> FEATURE:
<223> OTHER INFORMATION: IRS Peptide

<400> SEQUENCE: 62

Ala Ser Ser Asp Gly Glu Gly Thr Met Ser Arg Pro Ala Ser Val Asp
1               5                   10                  15

Gly Ser Pro Val Ser Pro Ser Thr Asn Arg
            20                  25

<210> SEQ ID NO 63
<211> LENGTH: 13
<212> TYPE: PRT
<213> ORGANISM: Artificial Sequence
<220> FEATURE:
<223> OTHER INFORMATION: IRS Peptide

<400> SEQUENCE: 63

Ser Val Ser Ala Pro Gln Gln Ile Ile Asn Pro Ile Arg
1               5                   10

<210> SEQ ID NO 64
<211> LENGTH: 28
<212> TYPE: PRT
<213> ORGANISM: Artificial Sequence
<220> FEATURE:
<223> OTHER INFORMATION: IRS Peptide

<400> SEQUENCE: 64

Leu Cys Leu Thr Ser Lys Thr Ile Ser Phe Val Lys Leu Asn Ser Glu
1               5                   10                  15

Ala Ala Ala Val Val Leu Gln Leu Met Asn Ile Arg
            20                  25

<210> SEQ ID NO 65
<211> LENGTH: 19
<212> TYPE: PRT
<213> ORGANISM: Artificial Sequence
<220> FEATURE:
<223> OTHER INFORMATION: IRS Peptide

<400> SEQUENCE: 65

Leu Glu Pro Ser Leu Pro His Pro His His Gln Val Leu Gln Pro His
1               5                   10                  15

Leu Pro Arg

<210> SEQ ID NO 66
<211> LENGTH: 13
<212> TYPE: PRT
<213> ORGANISM: Artificial Sequence
<220> FEATURE:
<223> OTHER INFORMATION: IRS Peptide

<400> SEQUENCE: 66

Leu Pro Gly His Arg His Ser Ala Phe Val Pro Thr Arg
1               5                   10

<210> SEQ ID NO 67
<211> LENGTH: 15
<212> TYPE: PRT
<213> ORGANISM: Artificial Sequence
<220> FEATURE:
<223> OTHER INFORMATION: IRS Peptide

<400> SEQUENCE: 67

```
Ser Ser Glu Asp Leu Ser Ala Tyr Ala Ser Ile Ser Phe Gln Lys
1               5                   10                  15
```

<210> SEQ ID NO 68
<211> LENGTH: 26
<212> TYPE: PRT
<213> ORGANISM: Artificial Sequence
<220> FEATURE:
<223> OTHER INFORMATION: IRS Peptide
<220> FEATURE:
<221> NAME/KEY: MOD_RES
<222> LOCATION: (12)..(12)
<223> OTHER INFORMATION: PHOSPHORYLATION

<400> SEQUENCE: 68

```
Pro Asp Ser Ser Thr Leu His Thr Asp Asp Gly Tyr Met Pro Met Ser
1               5                   10                  15

Pro Gly Val Ala Pro Val Pro Ser Gly Arg
            20                  25
```

<210> SEQ ID NO 69
<211> LENGTH: 31
<212> TYPE: PRT
<213> ORGANISM: Artificial Sequence
<220> FEATURE:
<223> OTHER INFORMATION: IRS Peptide
<220> FEATURE:
<221> NAME/KEY: MOD_RES
<222> LOCATION: (5)..(5)
<223> OTHER INFORMATION: PHOSPHORYLATION

<400> SEQUENCE: 69

```
Ser Pro Gly Glu Tyr Val Asn Ile Glu Phe Gly Ser Asp Gln Ser Gly
1               5                   10                  15

Tyr Leu Ser Gly Pro Val Ala Phe His Ser Ser Pro Ser Val Arg
            20                  25                  30
```

<210> SEQ ID NO 70
<211> LENGTH: 16
<212> TYPE: PRT
<213> ORGANISM: Artificial Sequence
<220> FEATURE:
<223> OTHER INFORMATION: IRS Peptide

<400> SEQUENCE: 70

```
Glu Gln Gln Gln Gln Gln Gln Pro Leu Leu His Pro Pro Glu Pro Lys
1               5                   10                  15
```

<210> SEQ ID NO 71
<211> LENGTH: 21
<212> TYPE: PRT
<213> ORGANISM: Artificial Sequence
<220> FEATURE:
<223> OTHER INFORMATION: IRS Peptide

<400> SEQUENCE: 71

```
His Ser Ser Ala Ser Phe Glu Asn Val Trp Leu Arg Pro Gly Glu Leu
1               5                   10                  15

Gly Gly Ala Pro Lys
            20
```

<210> SEQ ID NO 72
<211> LENGTH: 8
<212> TYPE: PRT
<213> ORGANISM: Artificial Sequence
<220> FEATURE:

```
<223> OTHER INFORMATION: IRS Peptide

<400> SEQUENCE: 72

Leu Glu Tyr Tyr Glu Asn Glu Lys
1               5

<210> SEQ ID NO 73
<211> LENGTH: 16
<212> TYPE: PRT
<213> ORGANISM: Artificial Sequence
<220> FEATURE:
<223> OTHER INFORMATION: IRS Peptide

<400> SEQUENCE: 73

Leu Asn Ser Glu Ala Ala Ala Val Val Leu Gln Leu Met Asn Ile Arg
1               5                   10                  15

<210> SEQ ID NO 74
<211> LENGTH: 7
<212> TYPE: PRT
<213> ORGANISM: Artificial Sequence
<220> FEATURE:
<223> OTHER INFORMATION: IRS Peptide

<400> SEQUENCE: 74

Leu Ser Leu Gly Asp Pro Lys
1               5

<210> SEQ ID NO 75
<211> LENGTH: 7
<212> TYPE: PRT
<213> ORGANISM: Artificial Sequence
<220> FEATURE:
<223> OTHER INFORMATION: IRS Peptide

<400> SEQUENCE: 75

Asn Leu Ile Gly Ile Tyr Arg
1               5

<210> SEQ ID NO 76
<211> LENGTH: 12
<212> TYPE: PRT
<213> ORGANISM: Artificial Sequence
<220> FEATURE:
<223> OTHER INFORMATION: IRS Peptide

<400> SEQUENCE: 76

Thr Gly Ile Ala Ala Glu Glu Val Ser Leu Pro Arg
1               5                   10

<210> SEQ ID NO 77
<211> LENGTH: 8
<212> TYPE: PRT
<213> ORGANISM: Artificial Sequence
<220> FEATURE:
<223> OTHER INFORMATION: IRS Peptide

<400> SEQUENCE: 77

His Leu Val Ala Leu Tyr Thr Arg
1               5
```

INSULIN RECEPTOR SUBSTRATE 1 (IRS1) PROTEIN SRM/MRM ASSAY

This application is a continuation of International Application No. PCT/US2010/061909, filed Dec. 22, 2010, which claims the benefit of U.S. Provisional Application 61/289,382, filed Dec. 22, 2009, both of which are entitled "Insulin Receptor Substrate 1 (IRS1) Protein SRM Assay" and name as an inventor David B. Krizman; each of which applications is herein incorporated by reference in its entirety.

INTRODUCTION

Specific peptides derived from subsequences of the Insulin Receptor Substrate 1 protein and which will be referred to as IRS1 are provided. The peptide sequence and fragmentation/transition ions for each peptide are particularly useful in a mass spectrometry-based Selected Reaction Monitoring (SRM), which can also be referred to as a Multiple Reaction Monitoring (MRM) assay, and will be referred to as SRM/MRM. Information about the use of peptides for SRM/MRM quantitative analysis of the IRS1 protein is described.

This SRM/MRM assay can be used to measure relative or absolute quantitative levels of one or more of the specific peptides from the IRS1 protein and therefore provide a means of measuring the amount of the IRS1 protein in a given protein preparation obtained from a biological sample by mass spectrometry.

More specifically, the SRM/MRM assay can measure these peptides directly in complex protein lysate samples prepared from cells procured from patient tissue samples, such as formalin fixed cancer patient tissue. Methods of preparing protein samples from formalin fixed tissue are described in U.S. Pat. No. 7,473,532, the contents of which are hereby incorporated by references in their entirety. The methods described in U.S. Pat. No. 7,473,532 may conveniently be carried out using Liquid Tissue™ reagents and protocol available from Expression Pathology Inc. (Rockville, Md.).

The most widely and advantageously available form of tissues from cancer patients tissue is formalin fixed, paraffin embedded tissue. Formaldehyde/formalin fixation of surgically removed tissue is by far and away the most common method of preserving cancer tissue samples worldwide and is the accepted convention for standard pathology practice. Aqueous solutions of formaldehyde are referred to as formalin. "100%" formalin consists of a saturated solution of formaldehyde (this is about 40% by volume or 37% by mass) in water, with a small amount of stabilizer, usually methanol to limit oxidation and degree of polymerization. The most common way in which tissue is preserved is to soak whole tissue for extended periods of time (8 hours to 48 hours) in aqueous formaldehyde, commonly termed 10% neutral buffered formalin, followed by embedding the fixed whole tissue in paraffin wax for long term storage at room temperature. Thus molecular analytical methods to analyze formalin fixed cancer tissue will be the most accepted and heavily utilized methods for analysis of cancer patient tissue.

Results from the SRM/MRM assay can be used to correlate accurate and precise quantitative levels of the IRS1 protein within the specific tissue samples (e.g., cancer tissue sample) of the patient or subject from whom the tissue (biological sample) was collected and preserved. This not only provides diagnostic information about the cancer, but also permits a physician or other medical professional to determine appropriate therapy for the patient. Such an assay that provides diagnostically and therapeutically important information about levels of protein expression in a diseased tissue or other patient sample is termed a companion diagnostic assay. For example, such an assay can be designed to diagnose the stage or degree of a cancer and determine a therapeutic agent to which a patient is most likely to respond.

SUMMARY

The assays described herein measure relative or absolute levels of specific unmodified peptides from the IRS1 protein and also can measure absolute or relative levels of specific modified peptides from the IRS1 protein. Examples of modifications include phosphorylated amino acid residues and glycosylated amino acid residues that are present on the peptides.

Relative quantitative levels of the IRS1 protein are determined by the SRM/MRM methodology for example by comparing SRM/MRM signature peak areas (e.g., signature peak area or integrated fragment ion intensity) of an individual IRS1 peptide in different samples. Alternatively, it is possible to compare multiple SRM/MRM signature peak areas for multiple IRS1 signature peptides, where each peptide has its own specific SRM/MRM signature peak, to determine the relative IRS1 protein content in one biological sample with the IRS1 protein content in one or more additional or different biological samples. In this way, the amount of a particular peptide, or peptides, from the IRS1 protein, and therefore the amount of the IRS1 protein, is determined relative to the same IRS1 peptide, or peptides, across 2 or more biological samples under the same experimental conditions. In addition, relative quantitation can be determined for a given peptide, or peptides, from the IRS1 protein within a single sample by comparing the signature peak area for that peptide by SRM/MRM methodology to the signature peak area for another and different peptide, or peptides, from a different protein, or proteins, within the same protein preparation from the biological sample. In this way, the amount of a particular peptide from the IRS1 protein, and therefore the amount of the IRS1 protein, is determined relative one to another within the same sample. These approaches generate quantitation of an individual peptide, or peptides, from the IRS1 protein to the amount of another peptide, or peptides, between samples and within samples wherein the amounts as determined by peak area are relative one to another, regardless of the absolute weight to volume or weight to weight amounts of the IRS1 peptide in the protein preparation from the biological sample. Relative quantitative data about individual signature peak areas between different samples are normalized to the amount of protein analyzed per sample. Relative quantitation can be performed across many peptides from multiple proteins and the IRS1 protein simultaneously in a single sample and/or across many samples to gain insight into relative protein amounts, one peptide/protein with respect to other peptides/proteins.

Absolute quantitative levels of the IRS1 protein are determined by, for example, the SRM/MRM methodology whereby the SRM/MRM signature peak area of an individual peptide from the IRS1 protein in one biological sample is compared to the SRM/MRM signature peak area of a spiked internal standard. In one embodiment, the internal standard is a synthetic version of the same exact IRS1 peptide that contains one or more amino acid residues labeled with one or more heavy isotopes. Such isotope labeled internal standards are synthesized so that when analyzed by mass spectrometry it generates a predictable and consistent SRM/MRM signature peak that is different and distinct from the native IRS1 peptide signature peak and which can be used as a comparator peak. Thus when the internal standard is spiked into a protein preparation from a biological sample in known amounts and analyzed by mass spectrometry, the SRM/MRM signature peak area of the native peptide is compared to the SRM/MRM signature peak area of the internal standard peptide, and this numerical comparison indicates either the absolute molarity and/or absolute weight of the native peptide present in the original protein preparation from the biological sample. Absolute quantitative data for fragment peptides are displayed according to the amount of protein analyzed per sample. Absolute quantitation can be performed across many peptides, and thus proteins, simultaneously in a single sample and/or across many samples to gain insight into absolute protein amounts in individual biological samples and in entire cohorts of individual samples.

The SRM/MRM assay method can be used to aid diagnosis of the stage of cancer, for example, directly in patient-derived tissue, such as formalin fixed tissue, and to aid in determining which therapeutic agent would be most advantageous for use in treating that patient. Cancer tissue that is removed from a patient either through surgery, such as for therapeutic removal of partial or entire tumors, or through biopsy procedures conducted to determine the presence or absence of suspected disease, is analyzed to determine whether or not a specific protein, or proteins, and which forms of proteins, are present in that patient tissue. Moreover, the expression level of a protein, or multiple proteins, can be determined and compared to a "normal" or reference level found in healthy tissue. Normal or reference levels of proteins found in healthy tissue may be derived from, for example, the relevant tissues of one or more individuals that do not have cancer. Alternatively, normal or reference levels may be obtained for individuals with cancer by analysis of relevant tissues not affected by the cancer. Assays of protein levels (e.g., IRS1 levels) can also be used to diagnose the stage of cancer in a patient or subject diagnosed with cancer by employing the IRS1 levels. Levels or amounts of proteins or peptides can be defined as the quantity expressed in moles, mass or weight of a protein or peptide determined by the SRM/MRM assay. The level or amount may be normalized to total the level or amount of protein or another component in the lysate analyzed (e.g., expressed in micromoles/microgram of protein or micrograms/microgram of protein). In addition, the level or amount of a protein or peptide may be determined on volume basis, expressed, for example, in micromolar or nanograms/microliter. The level or amount of protein or peptide as determined by the SRM/MRM assay can also be normalized to the number of cells analyzed. Information regarding IRS1 can thus be used to aid in determining stage or grade of a cancer by correlating the level of the IRS1 protein (or fragment peptides of the IRS1 protein) with levels observed in normal tissues. Once the stage and/or grade, and/or IRS1 protein expression characteristics of the cancer has been determined, that information can be matched to a list of therapeutic agents (chemical and biological) developed to specifically treat cancer tissue that is characterized by, for example, abnormal expression of the protein or protein(s) (e.g., IRS1) that were assayed. Matching information from an IRS1 protein assay to a list of therapeutic agents that specifically targets, for example, the IRS1 protein or cells/tissue expressing the protein, defines what has been termed a personalized medicine approach to treating disease. The assay methods described herein form the foundation of a personalized medicine approach by using analysis of proteins from the patient's own tissue as a source for diagnostic and treatment decisions.

DETAILED DESCRIPTION

In principle, any predicted peptide derived from the IRS1 protein, prepared for example by digesting with a protease of known specificity (e.g. trypsin), can be used as a surrogate reporter to determine the abundance of IRS1 protein in a sample using a mass spectrometry-based SRM/MRM assay. Similarly, any predicted peptide sequence containing an amino acid residue at a site that is known to be potentially modified in the IRS1 protein also might potentially be used to assay the extent of modification of the IRS1 protein in a sample.

IRS1 fragment peptides may be generated by a variety of means including by the use of the Liquid Tissue™ protocol provided in U.S. Pat. No. 7,473,532. The Liquid Tissue™ protocol and reagents are capable of producing peptide samples suitable for mass spectroscopic analysis from formalin fixed paraffin embedded tissue by proteolytic digestion of the proteins in the tissue/biological sample. In the Liquid Tissue™ protocol the tissue/biological is heated in a buffer for an extended period of time (e.g., from about 80° C. to about 100° C. for a period of time from about 10 minutes to about 4 hours) to reverse or release protein cross-linking. The buffer employed is a neutral buffer, (e.g., a Tris-based buffer, or a buffer containing a detergent). Following heat treatment the tissue/biological sample is treated with one or more proteases, including but not limited to trypsin, chymotrypsin, pepsin, and endoproteinase Lys-C for a time sufficient to disrupt the tissue and cellular structure of said biological sample and to liquefy said sample (e.g., a period of time from 30 minutes to 24 hours at a temperature from 37° C. to 65° C.). The result of the heating and proteolysis is a liquid, soluble, dilutable biomolecule lysate.

Surprisingly, it was found that many potential peptide sequences from the IRS1 protein are unsuitable or ineffective for use in mass spectrometry-based SRM/MRM assays for reasons that are not immediately evident. As it was not possible to predict the most suitable peptides for MRM/SRM assay, it was necessary to experimentally identify modified and unmodified peptides in actual Liquid Tissue™ lysates to develop a reliable and accurate SRM/MRM assay for the IRS1 protein. While not wishing to be bound by any theory, it is believed that some peptides might, for example, be difficult to detect by mass spectrometry as they do not ionize well or produce fragments distinct from other proteins, peptides may also fail to resolve well in separation (e.g., liquid chromatography), or adhere to glass or plastic ware.

IRS1 peptides found in various embodiments of this disclosure (e.g., Tables 1 and 2) were derived from the IRS1 protein by protease digestion of all the proteins within a complex Liquid Tissue™ lysate prepared from cells procured from formalin fixed cancer tissue. Unless noted otherwise, in each instance the protease was trypsin. The Liquid Tissue™ lysate was then analyzed by mass spectrometry to determine those peptides derived from the IRS1 protein that are detected and analyzed by mass spectrometry. Identification of a specific preferred subset of peptides for mass-spectrometric analysis is based on; 1) experimental determination of which peptide or peptides from a protein ionize in mass spectrometry analyses of Liquid Tissue™ lysates, and 2) the ability of the peptide to survive the protocol and experimental conditions used in preparing a Liquid Tissue™ lysate. This latter property extends not only to the amino acid sequence of the peptide but also to the ability of a modified amino acid residue within a peptide to survive in modified form during the sample preparation.

TABLE 1

| SEQ ID No. | Peptide Sequence |
|---|---|
| SEQ ID NO: 1 | EVWQVILKPKGLGQTK |
| SEQ ID NO: 2 | GLGQTKNLIGIYRLCLTSK |
| SEQ ID NO: 3 | GSGDYMPMSPKSVSAPQQIINPIR |
| SEQ ID NO: 4 | LCGAAGGLENGLNYIDLDLVK |
| SEQ ID NO: 5 | LNSEAAAVVLQLMNIRR |
| SEQ ID NO: 6 | LWTNGVGGHHSHVLPHPK |
| SEQ ID NO: 7 | NKHLVALYTR |
| SEQ ID NO: 8 | PKGLGQTKNLIGIYR |
| SEQ ID NO: 9 | RSIPLESCFNINK |
| SEQ ID NO: 10 | RTHSAGTSPTITHQK |
| SEQ ID NO: 11 | SQSSSNCSNPISVPLRRHHLNNPPPSQVGLTR |
| SEQ ID NO: 12 | SVSAPQQIINPIRR |
| SEQ ID NO: 13 | TISFVKLNSEAAAVVLQLMNIR |
| SEQ ID NO: 14 | VDTAAQTNSRLAR |
| SEQ ID NO: 15 | VIRADPQGCRR |
| SEQ ID NO: 16 | AASEAGGPARLEYYENEK |
| SEQ ID NO: 17 | AAWQESTGVEMGR |
| SEQ ID NO: 18 | AAWQESTGVEMGRLGPAPPGAASICR |
| SEQ ID NO: 19 | ADPQGCR |
| SEQ ID NO: 20 | AMSDEFRPRSK |
| SEQ ID NO: 21 | AREQQQQQQPLLHPPEPK |
| SEQ ID NO: 22 | ASSDGEGTMSRPASVDGSPVSPSTNR |
| SEQ ID NO: 23 | CPSQLQPAPR |
| SEQ ID NO: 24 | EEETGTEEYMK |
| SEQ ID NO: 25 | CTPGTGLGTSPALAGDEAASAADLDNR |
| SEQ ID NO: 26 | MDLGPGRR |
| SEQ ID NO: 27 | FFVLRAASEAGGPAR |
| SEQ ID NO: 28 | GGNGHRCTPGTGLGTSPALAGDEAASAADLDNR |
| SEQ ID NO: 29 | HHLNNPPPSQVGLTR |
| SEQ ID NO: 30 | HSAFVPTRSYPEEGLEMHPLER |
| SEQ ID NO: 31 | GSGDYMPMSPK |
| SEQ ID NO: 32 | VDTAAQTNSR |
| SEQ ID NO: 33 | KVGYLRK |
| SEQ ID NO: 34 | LARPTRLSLGDPK |
| SEQ ID NO: 35 | LHPPLNHSRSIPMPASRCSPSATSPVSLSSSSTSGHGSTSDCLFPR |
| SEQ ID NO: 36 | LLYAATADDSSSTSSDSLGGGYCGAR |
| SEQ ID NO: 37 | LSLGDPKASTLPR |
| SEQ ID NO: 38 | LSTSSGR |
| SEQ ID NO: 39 | PASVDGSPVSPSTNRTHAHR |
| SEQ ID NO: 40 | PDSSTLHTDDGYMPMSPGVAPVPSGR |
| SEQ ID NO: 41 | PGELGGAPK |
| SEQ ID NO: 42 | PRSKSQSSSNCSNPISVPLR |
| SEQ ID NO: 43 | PTRLSLGDPKASTLPR |
| SEQ ID NO: 44 | QSYVDTSPAAPVSYADMR |
| SEQ ID NO: 45 | RHHLNNPPPSQVGLTR |
| SEQ ID NO: 46 | HSSETFSSTPSATR |
| SEQ ID NO: 47 | RSRTESITATSPASMVGGK |
| SEQ ID NO: 48 | RSSEDLSAYASISFQK |
| SEQ ID NO: 49 | SIPLESCFNINK |
| SEQ ID NO: 50 | SKSQSSSNCSNPISVPLR |
| SEQ ID NO: 51 | SRTESITATSPASMVGGK |
| SEQ ID NO: 52 | SSASVSGSPSDGGFISSDEYGSSPCDFR |
| SEQ ID NO: 53 | SSEDLSAYASISFQKQPEDR |
| SEQ ID NO: 54 | SSFRSVTPDSLGHTPPA |
| SEQ ID NO: 55 | GEEELSNYICMGGK |
| SEQ ID NO: 56 | SVTPDSLGHTPPAR |
| SEQ ID NO: 57 | SYPEEGLEMHPLER |
| SEQ ID NO: 58 | TESITATSPASMVGGK |
| SEQ ID NO: 59 | VGNTVPFGAGAAVGGGGGSSSSSEDVK |
| SEQ ID NO: 60 | VNLSPNRNQSAK |
| SEQ ID NO: 61 | GSGDYMPMSPK |
| SEQ ID NO: 62 | ASSDGEGTMSRPASVDGSPVSPSTNR |
| SEQ ID NO: 63 | SVSAPQQIINPIR |
| SEQ ID NO: 64 | LCLTSKTISFVKLNSEAAAVVLQLMNIR |
| SEQ ID NO: 65 | LEPSLPHPHHQVLQPHLPR |
| SEQ ID NO: 66 | LPGHRHSAFVPTR |
| SEQ ID NO: 67 | SSEDLSAYASISFQK |
| SEQ ID NO: 68 | PDSSTLHTDDGY[phosphoyl]MPMSPGVAPVPSGR |
| SEQ ID NO: 69 | SPGEY[phosphoryl]VNIEFGSDQSGYLSGPVAFHSSPSVR |
| SEQ ID NO: 70 | EQQQQQQPLLHPPEPK |
| SEQ ID NO: 71 | HSSASFENVWLRPGELGGAPK |
| SEQ ID NO: 72 | LEYYENEK |
| SEQ ID NO: 73 | LNSEAAAVVLQLMNIR |

TABLE 1-continued

| Table 1 SEQ ID No. | Peptide Sequence |
|---|---|
| SEQ ID NO: 74 | LSLGDPK |
| SEQ ID NO: 75 | NLIGIYR |
| SEQ ID NO: 76 | TGIAAEEVSLPR |
| SEQ ID NO: 77 | HLVALYTR |

TABLE 2

| Table 2 SEQ ID NO. | Peptide sequence | Mono Isotopic Mass | Precursor Charge State | Precursor m/z | Transition m/z | Ion Type |
|---|---|---|---|---|---|---|
| SEQ ID NO: 22 | ASSDGEGTMSRPASVDGSPVSPSTNR | 2548.146 | 2 | 1275.07996 | 574.2938 | y5 |
| | | | 2 | | 857.447 | y8 |
| | | | 2 | | 1302.628 | y13 |
| | | | 2 | | 1373.665 | y14 |
| | | | 2 | | 1470.718 | y15 |
| | | | 3 | 850.388977 | 944.4791 | y9 |
| | | | 3 | | 1001.5 | y10 |
| | | | 3 | | 1116.527 | y11 |
| | | | 3 | | 1215.596 | y12 |
| | | | 3 | | 1302.628 | y13 |
| | | | 3 | | 1373.665 | y14 |
| | | | 3 | | 1470.718 | y15 |
| SEQ ID NO: 70 | EQQQQQQPLLHPPEPK | 1923.98 | 2 | 962.997009 | 930.5402 | y8 |
| | | | 2 | | 1027.593 | y9 |
| | | | 2 | | 1155.651 | y10 |
| | | | 2 | | 1283.71 | y11 |
| | | | 2 | | 1411.769 | y12 |
| | | | 3 | 642.333984 | 578.3294 | y10 |
| | | | 3 | | 704.3721 | y6 |
| | | | 3 | | 706.388 | y12 |
| | | | 3 | | 770.4172 | y13 |
| | | | 3 | | 817.4561 | y7 |
| | | | 3 | | 930.5402 | y8 |
| | | | 3 | | 1027.593 | y9 |
| | | | 3 | | 1155.651 | y10 |
| SEQ ID NO: 77 | HLVALYTR | 971.555 | 2 | 486.783997 | 552.3135 | y4 |
| | | | 2 | | 623.3506 | y5 |
| | | | 2 | | 722.419 | y6 |
| | | | 2 | | 835.5031 | y7 |
| | | | 2 | | 972.562 | y8 |

TABLE 2-continued

| Table 2 SEQ ID NO. | Peptide sequence | Mono Isotopic Mass | Precursor Charge State | Precursor m/z | Transition m/z | Ion Type |
|---|---|---|---|---|---|---|
| SEQ ID NO: 71 | HSSASFENVWLRPGELGGAPK | 2238.118 | 2 | 1120.06604 | 825.4459 | y9 |
| | | | 2 | | 1280.71 | y12 |
| | | | 2 | | 1379.779 | y13 |
| | | | 2 | | 1493.822 | y14 |
| | | | 3 | 747.046021 | 825.4459 | y9 |
| | | | 3 | | 981.5471 | y10 |
| | | | 3 | | 1008.021 | y19 |
| | | | 3 | | 1094.631 | y11 |
| | | | 3 | | 1280.71 | y12 |
| | | | 3 | | 1379.779 | y13 |
| | | | 3 | | 1493.822 | y14 |
| SEQ ID NO: 72 | LEYYENEK | 1086.487 | 2 | 544.25 | 390.1978 | y3 |
| | | | 2 | | 682.3037 | y5 |
| | | | 2 | | 845.367 | y6 |
| | | | 2 | | 974.4096 | y7 |
| | | | 2 | | 1087.494 | y8 |
| SEQ ID NO: 73 | LNSEAAAVVLQLMNIR | 1740.956 | 2 | 871.484985 | 774.4285 | y6 |
| | | | 2 | | 855.4565 | b8 |
| | | | 2 | | 887.5126 | y7 |
| | | | 2 | | 986.581 | y8 |
| | | | 2 | | 1085.649 | y9 |
| | | | 2 | | 1156.687 | y10 |
| | | | 2 | | 1227.724 | y11 |
| | | | 2 | | 1298.761 | y12 |
| | | | 2 | | 1427.803 | y13 |
| SEQ ID NO: 74 | LSLGDPK | 728.407 | 2 | 365.209992 | 416.2134 | y4 |
| | | | 2 | | 529.2975 | y5 |
| | | | 2 | | 616.3295 | y6 |
| | | | 2 | | 729.4136 | y7 |
| | | | 3 | 354.187012 | 406.2039 | y4 |
| | | | 3 | | 507.2516 | y5 |
| | | | 3 | | 594.2836 | y6 |
| | | | 3 | | 707.3677 | y7 |
| SEQ ID NO: 75 | NLIGIYR | 847.492 | 2 | 424.752991 | 451.2658 | y3 |
| | | | 2 | | 508.2873 | y4 |
| | | | 2 | | 621.3713 | y5 |

TABLE 2-continued

| Table 2 SEQ ID NO. | Peptide sequence | Mono Isotopic Mass | Precursor Charge State | Precursor m/z | Transition m/z | Ion Type |
|---|---|---|---|---|---|---|
| | | | 2 | | 734.4554 | y6 |
| | | | 2 | | 848.4983 | y7 |
| SEQ ID NO: 44 | QSYVDTSPAAPVSYADMR | 1956.889 | 2 | 979.450989 | 938.4395 | y8 |
| | | | 2 | | 1009.477 | y9 |
| | | | 2 | | 1080.514 | y10 |
| | | | 2 | | 1177.567 | y11 |
| | | | 2 | | 1264.599 | y12 |
| | | | 3 | 653.302979 | 655.2863 | y5 |
| | | | 3 | | 742.3183 | y6 |
| | | | 3 | | 841.3867 | y7 |
| | | | 3 | | 938.4395 | y8 |
| | | | 3 | | 1009.477 | y9 |
| | | | 3 | | 1080.514 | y10 |
| | | | 3 | | 1177.567 | y11 |
| SEQ ID NO: 63 | SVSAPQQIINPIR | 1421.799 | 2 | 711.906006 | 385.2552 | y3 |
| | | | 2 | | 499.2982 | y4 |
| | | | 2 | | 725.4663 | y6 |
| | | | 2 | | 853.5248 | y7 |
| | | | 2 | | 981.5834 | y8 |
| | | | 2 | | 1078.636 | y9 |
| | | | 2 | | 1149.673 | y10 |
| | | | 2 | | 1236.705 | y11 |
| | | | 2 | | 1335.774 | y12 |
| | | | 2 | | 1422.806 | y13 |
| SEQ ID NO: 57 | SYPEEGLEMHPLER | 1685.772 | 2 | 843.893005 | 514.2979 | y4 |
| | | | 2 | | 718.8453 | y12 |
| | | | 2 | | 911.4398 | y7 |
| | | | 2 | | 1024.524 | y8 |
| | | | 2 | | 1081.545 | y9 |
| | | | 2 | | 1210.588 | y10 |
| | | | 2 | | 1339.63 | y11 |
| | | | 2 | | 1436.683 | y12 |
| SEQ ID NO: 76 | TGIAAEEVSLPR | 1241.662 | 2 | 621.838013 | 272.1712 | y2 |
| | | | 2 | | 700.3983 | y6 |
| | | | 2 | | 829.4409 | y7 |
| | | | 2 | | 900.478 | y8 |

TABLE 2-continued

| Table 2 SEQ ID NO. | Peptide sequence | Mono Isotopic Mass | Precursor Charge State | Precursor m/z | Transition m/z | Ion Type |
|---|---|---|---|---|---|---|
| | | | 2 | | 971.5151 | y9 |
| | | | 2 | | 1084.599 | y10 |
| | | | 2 | | 1141.621 | y11 |
| | | | 2 | | 1242.668 | y12 |

Protein lysates from cells procured directly from formalin (formaldehyde) fixed tissue were prepared using the Liquid Tissue™ reagents and protocol that entails collecting cells into a sample tube via tissue microdissection followed by heating the cells in the Liquid Tissue™ buffer for an extended period of time. Once the formalin-induced cross linking has been negatively affected, the tissue/cells are then digested to completion in a predictable manner using a protease, as for example including but not limited to the protease trypsin. Each protein lysate is turned into a collection of peptides by digestion of intact polypeptides with the protease. Each Liquid Tissue™ lysate was analyzed (e.g., by ion trap mass spectrometry) to perform multiple global proteomic surveys of the peptides where the data was presented as identification of as many peptides as could be identified by mass spectrometry from all cellular proteins present in each protein lysate. An ion trap mass spectrometer or another form of a mass spectrometer that is capable of performing global profiling for identification of as many peptides as possible from a single complex protein/peptide lysate is employed. Ion trap mass spectrometers however may be the best type of mass spectrometer for conducting global profiling of peptides. Although SRM/MRM assay can be developed and performed on any type of mass spectrometer, including a MALDI, ion trap, or triple quadrupole, the most advantageous instrument platform for SRM/MRM assay is often considered to be a triple quadrupole instrument platform.

Once as many peptides as possible were identified in a single MS analysis of a single lysate under the conditions employed, then that list of peptides was collated and used to determine the proteins that were detected in that lysate. That process was repeated for multiple Liquid Tissue™ lysates, and the very large list of peptides was collated into a single dataset. That type of dataset can be considered to represent the peptides that can be detected in the type of biological sample that was analyzed (after protease digestion), and specifically in a Liquid Tissue™ lysate of the biological sample, and thus includes the peptides for specific proteins, such as for example the IRS1 protein.

In one embodiment, the IRS1 tryptic peptides identified as useful in the determination of absolute or relative amounts of the IRS1 receptor include one or more, two or more, three or more, four or more, five or more, six or more, eight or more, or ten or more of the peptides of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:38, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, and SEQ ID NO:77, each of which are listed in Table 1. Each of those peptides was detected by mass spectrometry in Liquid Tissue™ lysates prepared from formalin fixed, paraffin embedded tissue. Thus, each of the peptides in Table 1, or any combination of those peptides (e.g., one or more, two or more, three or more, four or more, five or more, six or more, eight or more, or ten or more of those peptides recited in Table 1, and particularly combinations with one or more of the peptides found in Table 2) are candidates for use in quantitative SRM/MRM assay for the IRS1 protein in human biological samples, including directly in formalin fixed patient tissue.

The IRS1 tryptic peptides listed in Table 1 include those detected from multiple Liquid Tissue™ lysates of multiple different formalin fixed tissues of different human organs including prostate, colon, and breast. Each of those peptides is considered useful for quantitative SRM/MRM assay of the IRS1 protein in formalin fixed tissue. Further data analysis of these experiments indicated no preference is observed for any specific peptides from any specific organ site. Thus, each of these peptides is believed to be suitable for conducting SRM/MRM assays of the IRS1 protein on a Liquid Tissue™ lysate from any formalin fixed tissue originating from any biological sample or from any organ site in the body.

In one embodiment the peptides in Table 1, or any combination of those peptides (e.g., one or more, two or more, three or more, four or more, five or more, six or more, eight or more, or ten or more of those peptides recited in Table 1, and particularly combinations with the peptides also found in Table 2) are assayed by methods that do not rely upon mass spectroscopy, including, but not limited to, immunological methods (e.g., Western blotting or ELISA). Regardless of how information directed to the amount of the peptide(s) (absolute or relative) is obtained, the information may be employed in any of the methods described herein, including indicating (diagnosing) the presence of cancer in a subject, determining the stage/grade/status of the cancer, providing a prognosis, or determining the therapeutics or treatment regimen for a subject/patient.

Embodiments of the present disclosure include compositions comprising one or more, two or more, three or more, four or more, five or more, six or more, eight or more, or ten or more of the peptides in Table 1. In some embodiments, the compositions comprise one or more, two or more, three or more, four or more, five or more, six or more, eight or more, or ten or more of the peptides in Table 2. Compositions comprising peptides may include one or more, two or more, three or more, four or more, five or more, six or more, eight or more, or ten or more peptides that are isotopically labeled. Each of the peptides may be labeled with one or more isotopes selected independently from the group consisting of: $^{18}O$, $^{17}O$, $^{34}S$, $^{15}N$, $^{13}C$, $^{2}H$ or combinations thereof. Compositions comprising peptides from the IRS1 protein, whether isotope labeled or not, do not need to contain all of the peptides from that protein (e.g., a complete set of tryptic peptides). In some embodiments the compositions do not contain one or more, two or more, three or more, four or more, five or more, six or more, eight or more, or ten or more peptides from IRS1, and particularly peptides appearing in Table 1 or Table 2. Compositions comprising peptides may be in the form of dried or lyophilized materials, liquid (e.g., aqueous) solutions or suspensions, arrays, or blots.

An important consideration for conducting an SRM/MRM assay is the type of instrument that may be employed in the analysis of the peptides. Although SRM/MRM assays can be developed and performed on any type of mass spectrometer, including a MALDI, ion trap, or triple quadrupole, the most advantageous instrument platform for SRM/MRM assay is often considered to be a triple quadrupole instrument platform. That type of a mass spectrometer may be considered to be the most suitable instrument for analyzing a single isolated target peptide within a very complex protein lysate that may consist of hundreds of thousands to millions of individual peptides from all the proteins contained within a cell.

In order to most efficiently implement SRM/MRM assay for each peptide derived from the IRS1 protein it is desirable to utilize information in addition to the peptide sequence in the analysis. That additional information may be used in directing and instructing the mass spectrometer (e.g. a triple quadrupole mass spectrometer), to perform the correct and focused analysis of specific targeted peptide(s), such that the assay may be effectively performed.

The additional information about target peptides in general, and about specific IRS1 peptides, may include one or more of the mono isotopic mass of the peptide, its precursor charge state, the precursor m/z value, the m/z transition ions, and the ion type of each transition ion. Additional peptide information that may be used to develop an SRM/MRM assay for the IRS1 protein is shown by example for twelve (12) of the IRS1 peptides from the list in Table 1 and is shown in Table 2. Similar additional information described for these twelve (12) IRS1 peptides shown by example in Table 2 may be prepared, obtained, and applied to the analysis of the other peptides contained in Table 1.

The method described below was used to: 1) identify candidate peptides from the IRS1 protein that can be used for a mass spectrometry-based SRM/MRM assay for the IRS1 protein, 2) develop individual SRM/MRM assay, or assays, for target peptides from the IRS1 protein in order to correlate and 3) apply quantitative assays to cancer diagnosis and/or choice of optimal therapy.

Assay Method
1. Identification of SRM/MRM candidate fragment peptides for the IRS1 protein
   a. Prepare a Liquid Tissue™ protein lysate from a formalin fixed biological sample using a protease or proteases, (that may or may not include trypsin), to digest proteins
   b. Analyze all protein fragments in the Liquid Tissue™ lysate on an ion trap tandem mass spectrometer and identify all fragment peptides from the IRS1 protein, where individual fragment peptides do not contain any peptide modifications such as phosphorylations or glycosylations
   c. Analyze all protein fragments in the Liquid Tissue™ lysate on an ion trap tandem mass spectrometer and identify all fragment peptides from the IRS1 protein that carry peptide modifications such as for example phosphorylated or glycosylated residues
   d. All peptides generated by a specific digestion method from the entire, full length IRS1 protein potentially can be measured, but preferred peptides used for development of the SRM/MRM assay are those that are identified by mass spectrometry directly in a complex Liquid Tissue™ protein lysate prepared from a formalin fixed biological sample
   e. Peptides that are specifically modified (phosphorylated, glycosylated, etc.) in patient tissue and which ionize, and thus detected, in a mass spectrometer when analyzing a Liquid Tissue™ lysate from a formalin fixed biological sample are identified as candidate peptides for assaying peptide modifications of the IRS1 protein
2. Mass Spectrometry Assay for Fragment Peptides from IRS1 Protein
   a. SRM/MRM assay on a triple quadrupole mass spectrometer for individual fragment peptides identified in a Liquid Tissue™ lysate is applied to peptides from the IRS1 protein
      i. Determine optimal retention time for a fragment peptide for optimal chromatography conditions including but not limited to gel electrophoresis, liquid chromatography, capillary electrophoresis, nano-reversed phase liquid chromatography, high performance liquid chromatography, or reverse phase high performance liquid chromatography
      ii. Determine the mono isotopic mass of the peptide, the precursor charge state for each peptide, the precursor m/z value for each peptide, the m/z transition ions for each peptide, and the ion type of each transition ion for each fragment peptide in order to develop an SRM/MRM assay for each peptide.
      iii. SRM/MRM assay can then be conducted using the information from (i) and (ii) on a triple quadrupole mass spectrometer where each peptide has a characteristic and unique SRM/MRM signature peak that precisely defines the unique SRM/MRM assay as performed on a triple quadrupole mass spectrometer
   b. Perform SRM/MRM analysis so that the amount of the fragment peptide of the IRS1 protein that is detected, as a function of the unique SRM/MRM signature peak area from an SRM/MRM mass spectrometry analysis, can indicate both the relative and absolute amount of the protein in a particular protein lysate.
      i. Relative quantitation may be achieved by:
         1. Determining increased or decreased presence of the IRS1 protein by comparing the SRM/MRM signature peak area from a given IRS1 peptide detected in a Liquid Tissue™ lysate from one formalin fixed biological sample to the same SRM/MRM signature peak area of the same IRS1 fragment peptide in at least a second, third, fourth or more Liquid Tissue™ lysates from least a second, third, fourth or more formalin fixed biological samples
         2. Determining increased or decreased presence of the IRS1 protein by comparing the SRM/MRM signature peak area from a given IRS1 peptide detected in a Liquid Tissue™ lysate from one formalin fixed biological sample to SRM/MRM signature peak areas developed from fragment peptides from other proteins, in other samples derived from different and separate biological sources, where the SRM/MRM signature peak area comparison between the 2 samples for a peptide fragment are normalized to amount of protein analyzed in each sample.
3. Determining increased or decreased presence of the IRS1 protein by comparing the SRM/MRM signature peak area for a given IRS1 peptide to the SRM/MRM signature peak areas from other fragment peptides derived from different proteins within the same Liquid Tissue™ lysate from the formalin fixed biological sample in order to normalize changing levels of IRS1 protein to levels of other proteins that do not change their levels of expression under various cellular conditions.
4. These assays can be applied to both unmodified fragment peptides and for modified fragment peptides of the IRS1 protein, where the modifications include but are not limited to phosphorylation and/or glycosylation, and where the relative levels of modified peptides are determined in the same manner as determining relative amounts of unmodified peptides.
ii. Absolute quantitation of a given peptide may be achieved by comparing the SRM/MRM signature peak area for a given fragment peptide from the IRS1 protein in an individual biological sample to the SRM/MRM signature peak area of an internal fragment peptide standard spiked into the protein lysate from the biological sample
1. The internal standard is a labeled synthetic version of the fragment peptide from the IRS1 protein that is being interrogated. This standard is spiked into a sample in known amounts, and the SRM/MRM signature peak area can be determined for both the internal fragment peptide standard and the native fragment peptide in the biological sample separately, followed by comparison of both peak areas
2. This can be applied to unmodified fragment peptides and modified fragment peptides, where the modifications include but are not limited to phosphorylation and/or glycosylation, and where the absolute levels of modified peptides can be determined in the same manner as determining absolute levels of unmodified peptides.
3. Apply Fragment Peptide Quantitation to Cancer Diagnosis and Treatment
a. Perform relative and/or absolute quantitation of fragment peptide levels of the IRS1 protein and demonstrate that the previously-determined association, as well understood in the field of cancer, of IRS1 protein expression to the stage/grade/status of cancer in patient tumor tissue is confirmed
b. Perform relative and/or absolute quantitation of fragment peptide levels of the IRS1 protein and demonstrate correlation with clinical outcomes from different treatment strategies, wherein this correlation has already been demonstrated in the field or can be demonstrated in the future through correlation studies across cohorts of patients and tissue from those patients. Once either previously established correlations or correlations derived in the future are confirmed by this assay then the assay method can be used to determine optimal treatment strategy The information shown in Table 2 is necessary to develop an SRM/MRM assay for quantitation of the IRS1 protein on a triplequadrupole mass spectrometer. Specific and unique characteristics about these IRS1 peptides were developed by analysis of all IRS1 peptides on both an ion trap and triple quadrupole mass spectrometers. That information includes the monoisotopic mass of the peptide, its precursor charge state, the precursor m/z value, the transition m/z values of the precursor, and the ion types of each of the identified transitions. That information must be determined experimentally for each and every candidate SRM/MRM peptide directly in Liquid Tissue™ lysates from formalin fixed tissue; because, interestingly, not all peptides from the IRS1 protein can be detected in such lysates using SRM/MRM as described herein, indicating that IRS1 peptides not detected cannot be considered candidate peptides for developing an SRM/MRM assay for use in quantitating peptides/proteins directly in Liquid Tissue™ lysates from formalin fixed tissue.

Utilizing this information, quantitative SRM/MRM assays can be developed for the IRS1 protein, and assessment of IRS1 protein levels in tissues based on analysis of formalin fixed patient-derived tissue can provide diagnostic, prognostic, and therapeutically-relevant information about each particular patient. In one embodiment, this disclosure describes a method for measuring the level of the IRS1 protein in a biological sample, comprising detecting and/or quantifying the amount of one or more modified or unmodified IRS1 fragment peptides in a protein digest prepared from said biological sample using mass spectrometry; and calculating the level of modified or unmodified IRS1 protein in said sample; and wherein said level is a relative level or an absolute level. In a related embodiment, quantifying one or more IRS1 fragment peptides comprises determining the amount of the each of the IRS1 fragment peptides in a biological sample by comparison to an added internal standard peptide of known amount, wherein each of the IRS1 fragment peptides in the biological sample is compared to an internal standard peptide having the same amino acid sequence. In some embodiments the internal standard is an isotopically labeled internal standard peptide comprises one or more heavy stable isotopes selected from $^{18}O$, $^{17}O$, $^{34}S$, $^{15}N$, $^{13}C$, $^{2}H$ or combinations thereof.

The method for measuring the level of the IRS1 protein in a biological sample described herein (or fragment peptides as surrogates thereof) may be used as a diagnostic indicator of cancer in a patient or subject. In one embodiment, the results from measurements of the level of the IRS1 protein may be employed to determine the diagnostic stage/grade/status of a cancer by correlating (e.g., comparing) the level of IRS1 receptor found in a tissue with the level of that protein found in normal and/or cancerous or precancerous tissues.

What is claimed is:

1. A method for measuring the level of the Insulin Receptor Substrate 1 (IRS 1) protein in a human biological sample of formalin fixed tissue, comprising detecting and quantifying the amount of an IRS 1 fragment peptide in a protein digest prepared from said biological sample using mass spectrometry; and calculating the level of IRS 1 protein in said sample; wherein said protein digest comprises a protease digest, wherein the tissue is obtained from a tumor, wherein said IRS 1 fragment peptide has the sequence set forth in SEQ ID NO:76, wherein quantifying said IRS 1 fragment peptide comprises determining the amount of said IRS 1 fragment peptide in a biological sample by comparison to an added internal standard peptide of known amount, wherein said IRS 1 fragment peptide in the biological sample is compared to an internal standard peptide having the same amino acid sequence, wherein the internal standard peptide is an isotopically labeled peptide, and wherein said level of IRS1 protein in said biological sample is an absolute level.

2. The method of claim 1, further comprising the step of fractionating said protein digest prior to detecting and quantifying the amount of said IRS1 fragment peptide.

3. The method of claim 1, wherein the tissue is paraffin embedded tissue.

* * * * *